US00PP30349P2

(12) United States Plant Patent
Olesen

(10) Patent No.: US PP30,349 P2
(45) Date of Patent: Apr. 9, 2019

(54) MINIATURE ROSE PLANT NAMED 'POULPAR109'

(50) Latin Name: *Rosa hybrida*
Varietal Denomination: Poulpar109

(71) Applicant: Mogens Nyegaard Olesen, Fredensborg (DK)

(72) Inventor: Mogens Nyegaard Olesen, Fredensborg (DK)

(73) Assignee: Poulsen Roser A/S, Fredensborg (DK)

( * ) Notice: Subject to any disclaimer, the term of this patent is extended or adjusted under 35 U.S.C. 154(b) by 0 days.

(21) Appl. No.: 15/731,968

(22) Filed: Sep. 5, 2017

(51) Int. Cl.
*A01H 5/02* (2018.01)

(52) U.S. Cl.
USPC ..... Plt./119

(58) Field of Classification Search
USPC ..... Plt./116, 118, 119, 123, 125, 126, 141, Plt./145, 146
CPC ..... A01H 5/02; A01H 5/0222; A01H 6/749
See application file for complete search history.

(56) References Cited

PUBLICATIONS

Poulsen Roser A/S for Pina retrieved on Jul. 31, 2018, retrieved from the Internet at http://de.poulsenroses.eu/sortiment/rosen-collectionen/parade/pina.aspx, 2 pp. (Year: 2018).*

* cited by examiner

*Primary Examiner* — June Hwu

(57) ABSTRACT

A new garden rose plant of the Miniature class which has abundant, pink orange blend flowers and attractive foliage. This new and distinct variety has shown to be uniform and stable in the resulting generations from asexual propagation.

2 Drawing Sheets

Botanical designation: *Rosa hybrida.*
Variety denomination: 'Poulpar109'.

SUMMARY OF THE INVENTION

The present invention constitutes a new and distinct variety of rose plant which originated from a controlled crossing between the female seed parent, an unnamed seedling, and the male pollen parent, also an unnamed seedling. Both of the parent varieties are non-patented.

The two parents were crossed during the summer of 2011 and the resulting seeds were planted in a controlled environment in Fredensborg, Denmark. The new variety, named 'Poulpar109', originated as a single seedling from the stated cross.

The new variety may be distinguished from its male pollen parent and female seed parent primarily by the following characteristics. The male pollen parent plant has orange flowers while the new variety has pink orange blend flowers. The female seed parent plant has golden yellow flowers while the new variety has pink orange blend flowers.

The objective of the hybridization of this rose variety was to create a new and distinct variety with unique qualities, such as:

1. Uniform and abundant pink orange blend flowers;
2. Vigorous, but compact growth when propagated on its own roots;
3. Exceptional disease resistance.

This combination of qualities is not present in previously available commercial cultivars of this type, known to the inventor, and distinguish 'Poulpar109' from all other varieties of which we are aware.

As part of the rose development program, Mogens N. Olesen germinated the seeds from the aforementioned hybridization during winter of 2011 and conducted evaluations on the resulting seedlings in a controlled environment in Fredensborg, Denmark. 'Poulpar109' was selected in the spring of 2012 by the inventor as a single plant from the progeny of the aforementioned hybridization.

Asexual reproduction of 'Poulpar109' by rooted cuttings was first done by Mogens N. Olesen in the nursery in Fredensborg, Denmark in July, 2012. This initial and other subsequent asexual propagations conducted in controlled environments have demonstrated that the characteristics of 'Poulpar109' are true to type and are transmitted from one generation to the next.

DESCRIPTION OF THE DRAWING

The accompanying color illustrations show as true as is reasonably possible to obtain in color photographs of this type, the typical characteristics of the buds, flowers, leaves, and stems, of 'Poulpar109'.

Specifically illustrated in FIG. 1 of the drawings are open flowers, petals and sepals detached, and reproductive flower parts.

Figure 1:
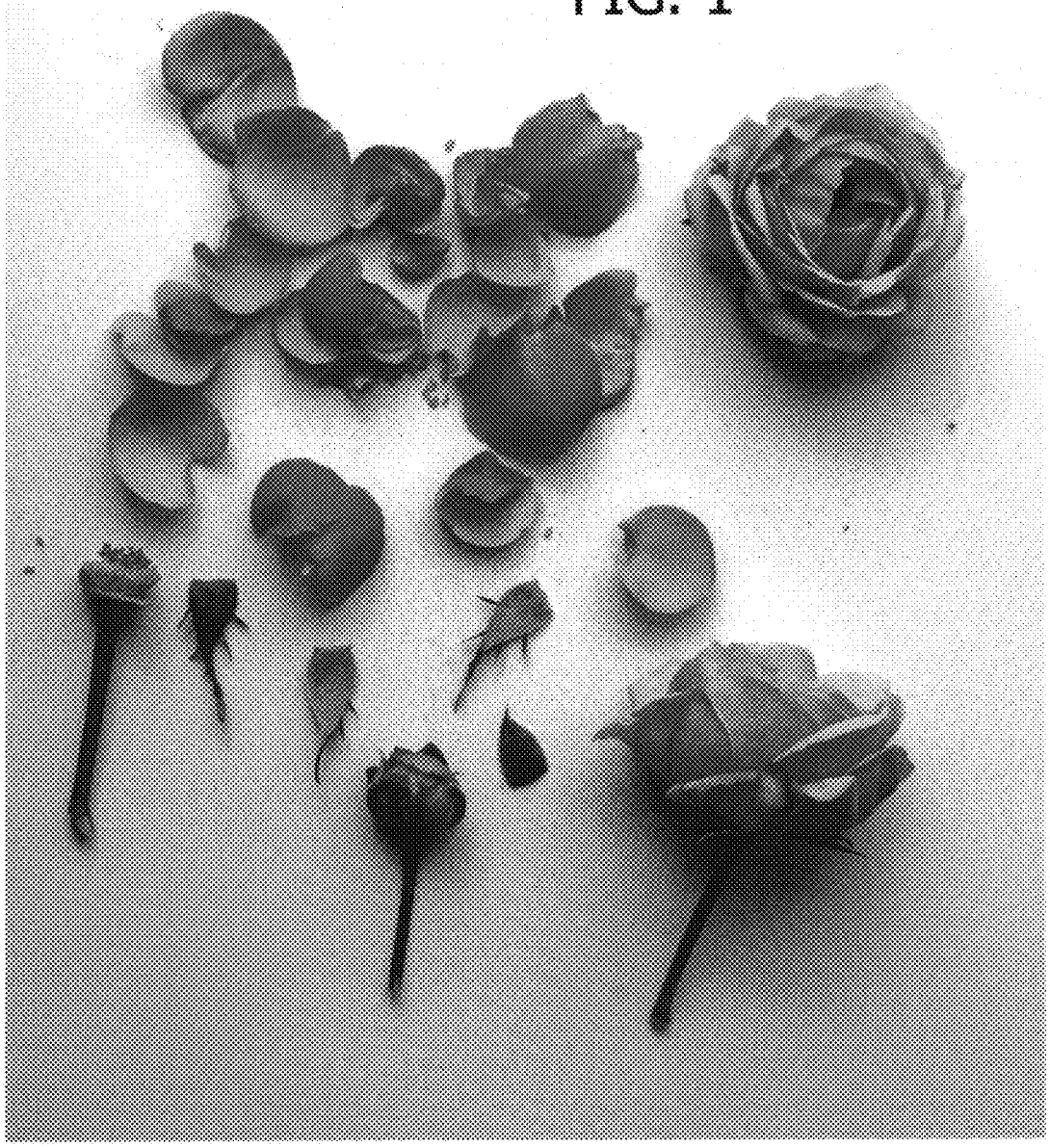
Figure 2:
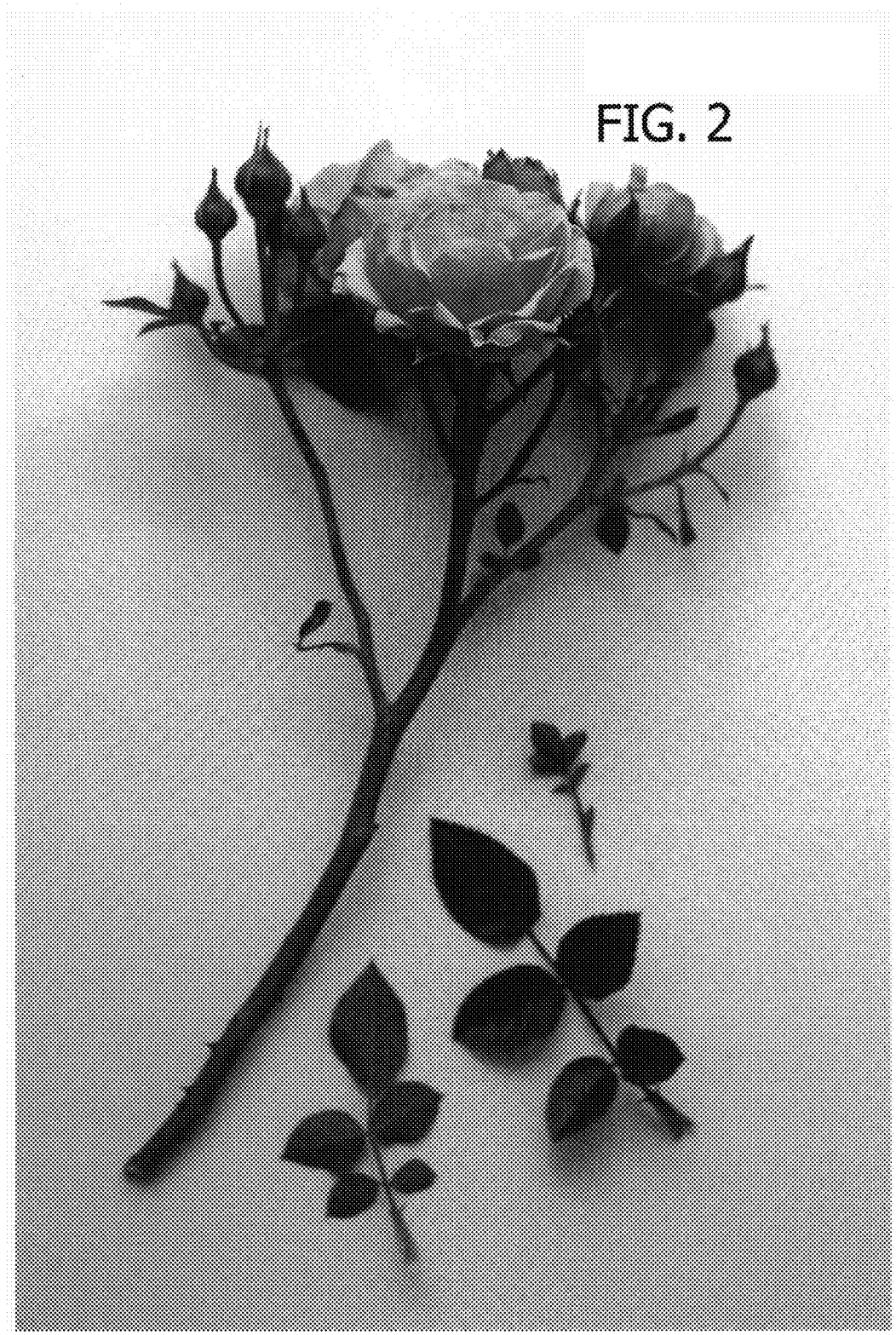

Specifically illustrated in FIG. 2 of the drawings are a cluster of flowers on a branch and leaves. Plants shown are 2 years of age.

Detailed Description of the Variety

The following is a description of 'Poulpar109', as observed in its growth in a field nursery in Marion County, Oreg. Observed plants are 2 years of age, and were grown on their own roots. Color references are made using The Royal Horticultural Society (London, England) Colour Chart, 2001, except where common terms of color are used.

For a comparison, several physical characteristics of the rose variety 'Poulpollo', U.S. Plant Pat. No. 11,539 are compared to 'Poulpar109' in Chart 1.

CHART 1

| | 'Poulpar109' | 'Poulpollo' |
|---|---|---|
| Petal Count | 30 | 30-35 |
| Flower Diameter | 55 mm | 40-45 mm |
| General Tonality of Flower Color | Orange Group 27C and Orange Group 29B, and Red Group 38A | Blend of Greyed-Orange Group 170C and Orange Group 28D-29D |

FLOWER AND FLOWER BUD

Blooming habit: Continuous.

Flower bud:

*Size.*—Upon opening, 20 mm in length from base of receptacle to end of bud. Bud diameter is 15 mm.

*Bud form.*—Ovoid.

*Bud color.*—As sepals divide petals are Red Group 43C and Red Group 46C.

*Sepal inner surface.*—Color: Yellow-Green Group 146D. Surface: Lightly pubescent.

*Sepal outer surface.*—Color: Yellow-Green Group 144A with intonations of Greyed-Red Group 181B. Texture: Smooth.

*Sepal shape.*—Apex: Cirrhose. Base: Flat at union with receptacle.

*Sepal margin.*—Margins have moderate foliaceous appendages on three of the five sepals.

*Sepal size.*—30 mm long, 9 mm wide.

*Receptacle.*—Texture: Smooth. Size: 4 mm in height, 7 mm wide. Color: Yellow-Green Group 144A. Shape: Funnel.

*Pedicel.*—Surface: Smooth. Length: About 35 mm. Diameter: 2 mm on average. Color: Yellow-Green Group 144A with intonations of Greyed-Red Group 181B. Strength: Strong.

*Peduncle.*—Length: 2 to 10 cm. Diameter: About 3 mm. Color: Yellow-Green Group 145A. Texture: Smooth.

Flower bud development: Flower buds are borne in clusters of 3 to 5 flower buds on each peduncle. Overall, each flowering branch exhibits about 20 flowers.

Flower bloom:

*Fragrance.*—Light floral.

*Duration.*—The blooms have a duration on the plant of approximately 20 days. Petals fall cleanly away from plant after flowers have fully matured.

*Size.*—Flower diameter is 55 mm when open. Flower depth is 27 mm.

*Flower shape.*—Rosette, somewhat globular in shape, with many slightly overlapping petals of different sizes.

*Shape of flower, side view.*—The upper portion is flattened convex. The lower portion is flat.

Petalage: Double flower. Under normal conditions, flowers have about 30 petals.

General tonality of flower: Open flowers are Orange Group 27C and Orange Group 29B, and Red Group 38A.

Petal color:

*Upon opening, and after opening, outer petals.*—Upper surface: Yellow-Orange Group 19C at marginal and middle zone. Towards basal zone Yellow Group 3C. Lower surface: Red Group 54B and Red Group 36C with additional intonations of Orange Group 26C.

*Upon opening, and after opening, inner petals.*—Upper surface: Yellow-Orange Group 19B. Lower surface: Red Group 37A with intonations of Orange Group 29C.

*Basal petal spots, upon and after opening.*—Upper surface: A small expression of Yellow Group 3C. Lower surface: A small expression of Yellow Group 3C.

Petals:

*Petal reflex.*—Outer petals are partially reflexed.

*Margin.*—Some petals are entire and uniform. Other petals exhibit clefts at the apex of the margin. Moderate to strong undulations.

*Shape.*—Rounded. Apex shape: Rounded. Base shape: Obtuse.

*Size.*—23 mm (l)×28 mm (w).

*Texture.*—Smooth.

*Thickness.*—Average.

Petaloids:

*Size.*—12 mm (l) by 6 mm (w).

*Quantity.*—About 6.

*Shape.*—Elliptical with an acute base and rounded apex.

*Color.*—Upper surface is Yellow-Orange Group 19B. Lower surface is Red Group 37A with intonations of Orange Group 29C.

Reproductive flower parts:

*Pollen.*—None observed.

*Anthers.*—Size: 2 mm in length. Color: Yellow Group 13B. Quantity: 50 on average.

*Filaments.*—Color: Yellow-White Group 158C. Length: 3 mm.

*Pistils.*—Length: 5 mm. Quantity: 38 on average.

*Stigmas.*—Color: Red Group 43B.

*Styles.*—Color: Yellow Group 5D.

*Location of stigmas.*—Superior in location relative to the length of the filaments and the height of the anthers.

*Hips.*—None Observed.

PLANT

Plant growth: Upright, bushy. Plants are 30 cm in height, and 30 cm wide.

Stems:

*Color of juvenile growth.*—Yellow-Green Group 144B.

*Color of mature growth.*—Yellow-Green Group 144A.

*Length.*—Canes are about 15 cm from the base of the plant to the flowering portion.

*Diameter.*—About 5 mm.

*Internodes.*—On mature canes about 37 mm between nodes.

*Surface texture.*—Young wood: Smooth. Older wood: Smooth.

Long prickles:

*Incidence.*—4 prickles per 10 cm of stem.

*Size.*—Average length of prickles on mature stems is 4 mm.

*Shape.*—Upper portion is concave. Lower portion is concave.

*Color.*—Juvenile prickles: Greyed-Red Group 179A. Mature prickles: Greyed-Red Group 179A.

Plant foliage:

*Compound leaf.*—105 mm (l)×60 (w).

*Quantity.*—3 leaves per 10 cm of stem on average.

*Color of juvenile foliage.*—Upper side: Yellow-Green Group 144A with intonations of Greyed-Red Group 179A. Lower side: Yellow-Green Group 144B with intonations of Greyed-Red Group 179A.

*Color of mature foliage.*—Upper side: Yellow-Green Group 147A. Lower side: Yellow-Green Group 146B.

Plant leaves and leaflets:

*Stipules.*—Size: 18 mm long, 3 mm wide. Quantity: 2 per compound leaf. Shape: Linear, slightly broad based with outward extending apices. Margins: Finely serrated. Color: Yellow-Green Group 144A.

*Petiole.*—Length: 22 mm. Diameter: About 2 mm. Upper surface color: Yellow-Green Group 144A with intonations of Greyed-Red Group 179B. Lower surface color: Yellow-Green Group 144A. Surface Texture: Smooth.

*Rachis.*—Length: 35 mm. Upper surface color: Yellow-Green Group 144A with intonations of Greyed-Red Group 179B. Lower surface color: Yellow-Green Group 144A. Surface Texture: Smooth.

*Leaflet.*—Quantity: Normally 5 leaflets. Margins: Serrated. Undulations absent. Size: Terminal leaflets are about 35 mm long, 23 mm wide. Shape: Generally elliptical. Base: Rounded. Apex: Acute. Texture: Smooth. Thickness: Average. Arrangement: Odd pinnate. Venation: Reticulate. Glossiness: Moderately glossy.

Disease resistance: Above average resistance to powdery mildew *Sphaerotheca pannosa* var *rosae*, downy mildew *Peronospora sparsa*, rust *Phragmidium* spp., black spot *Diplocarpon rosae*, and *Botrytis cinerea* under normal growing conditions.

Cold hardiness: The variety is tolerant to USDA Cold Hardiness Zone 6.

Heat tolerance: The variety has been found to be suitable for climate conditions found in the American Horticulture Society heat zone 7.

We claim:

1. A new and distinct variety of rose plant of the Miniature rose class named 'Poulpar109', substantially as illustrated and described herein, due to its abundant pink orange flowers, disease resistance, and extended period of bloom.

* * * * *